United States Patent
Claypool et al.

(10) Patent No.: US 12,336,702 B2
(45) Date of Patent: Jun. 24, 2025

(54) AUTO-SUTURED ALLOGRAFT

(71) Applicant: WRIGHT MEDICAL TECHNOLOGY, INC., Memphis, TN (US)

(72) Inventors: Jody Claypool, Warsaw, IN (US); Shawn E. McGinley, Arlington, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 473 days.

(21) Appl. No.: 17/787,615

(22) PCT Filed: Feb. 2, 2021

(86) PCT No.: PCT/US2021/016138
§ 371 (c)(1),
(2) Date: Jun. 21, 2022

(87) PCT Pub. No.: WO2021/178086
PCT Pub. Date: Sep. 10, 2021

(65) Prior Publication Data
US 2022/0409199 A1 Dec. 29, 2022

Related U.S. Application Data

(60) Provisional application No. 62/984,467, filed on Mar. 3, 2020.

(51) Int. Cl.
*A61B 17/04* (2006.01)
*A61B 17/06* (2006.01)

(52) U.S. Cl.
CPC .. *A61B 17/0469* (2013.01); *A61B 2017/0472* (2013.01); *A61B 2017/06076* (2013.01)

(58) Field of Classification Search
CPC ...... A61B 17/0469; A61B 2017/06076; A61B 2017/0472
See application file for complete search history.

(56) References Cited

U.S. PATENT DOCUMENTS 5,437,681 A   8/1995 Meade et al.
6,015,416 A * 1/2000 Stefanchik ............. A61B 17/11
                                                     606/1

(Continued)

FOREIGN PATENT DOCUMENTS

EP       0938870 B1    5/2006

OTHER PUBLICATIONS

International Search Report and Written Opinion issued in connection with International Patent Application No. PCT/US2021/016138, 14 pages, Apr. 21, 2021.

(Continued)

*Primary Examiner* — Erin McGrath
(74) *Attorney, Agent, or Firm* — DUANE MORRIS LLP

(57) ABSTRACT

An auto-suture device includes a spiral drive mechanism having a first spiral drive tube including a cylindrical body having an internal surface defining a first travel path, a second spiral drive tube moveably coupled to the first spiral drive tube, and a first spiral drive element including a drive interface and a needle drive. The needle drive is sized and configured to be received within the first travel path defined by the first spiral drive tube.

16 Claims, 20 Drawing Sheets

(56) References Cited

U.S. PATENT DOCUMENTS

| | | | |
|---|---|---|---|
| 2001/0018592 A1* | 8/2001 | Schaller | A61B 17/064 606/228 |
| 2007/0060931 A1 | 3/2007 | Hamilton et al. | |
| 2011/0015654 A1 | 1/2011 | Tsuang et al. | |
| 2014/0236189 A1 | 8/2014 | Melsheimer et al. | |
| 2016/0345962 A1 | 12/2016 | Marczyk et al. | |
| 2019/0388087 A1 | 12/2019 | Almodovar | |

OTHER PUBLICATIONS

Extended European Search Report issued in connection with European Patent Application No. 21764940.9, Nov. 17, 2023, 10 pages.

* cited by examiner

AUTO-SUTURED ALLOGRAFT

CROSS-REFERENCE TO RELATED APPLICATIONS

This application is a National Stage Application, filed under 35 U.S.C. 371, of International Patent Application No. PCT/US2021/016138, filed on Feb. 2, 2021, which claims priority to U.S. Provisional Patent Application No. 62/984,467, filed on Mar. 3, 2020, the entire contents of which are incorporated herein by reference.

BACKGROUND

An allograft includes bone, tendon, skin, and/or other types of tissue transplanted from one person to another. Allografts are used in a variety of medical treatments, including, but not limited to, knee replacements, bone grafts, spinal fusions, eye surgery, and skin grafts for the severely burned. Allografts come from voluntarily donated human tissue obtained from donor-derived, living-related, or living-unrelated donors and can help patients regain mobility, restore function, enjoy a better quality of life, and save lives.

When using an allograft, current systems require stitching of the ends of the allograft to enable connection to bone fixtures. For example, surgeons may be required to stitch one or both ends of the allograft and trim the suture length to a predetermined length. Current solutions prevent a pre-sutured end as trimming of a pre-sutured end may result in removal of suture required for connection to the bone fixtures.

SUMMARY

In various embodiments, an auto-suture device is disclosed. The auto-suture device includes a spiral drive mechanism having a first spiral drive tube including a cylindrical body having an internal surface defining a first travel path, a second spiral drive tube moveably coupled to the first spiral drive tube, and a first spiral drive element including a drive interface and a needle drive. The needle drive is sized and configured to be received within the first travel path defined by the first spiral drive tube.

In various embodiments, an auto-suture device is disclosed. The auto-suture device include a spiral drive mechanism and a handle. The spiral drive mechanism includes a first spiral drive tube having a cylindrical body having an internal surface defining a first travel path and a second spiral drive tube having a cylindrical body having an internal surface defining a second travel path. The first spiral drive tube is coupled to the second spiral drive tube by a pivot element. The spiral drive mechanism further includes a first spiral drive element and a second spiral drive element each having a drive interface and a needle drive. The needle drive of the first spiral drive element is sized and configured to be received within the first travel path defined by the first spiral drive tube and the needle drive of the second spiral drive element is sized and configured to be received within the second travel path defined by the second spiral drive tube. The handle is configured to be fixedly coupled to the drive interface of the first spiral drive tube. Rotation of the handle is configured to cause simultaneous advancement of the first spiral drive element and the second spiral drive element within the first travel path and the second travel path, respectively.

In various embodiments, a method of suturing an allograft is disclosed. The method includes positioning a portion of an allograft between a first spiral drive tube and a second spiral drive tube of a spiral drive mechanism, rotating a first spiral drive element within the first spiral drive tube to advance the first spiral drive element along a travel path defined by an inner surface of the first spiral drive tube, and coupling a suture to the portion of the allograft positioned between the first spiral drive tube and the second spiral drive tube. Rotation of the spiral drive element causes a needle to penetrate the allograft and the suture is coupled to the needle. The allograft is released from the spiral drive mechanism by pivoting the first spiral drive tube and the second spiral drive tube.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
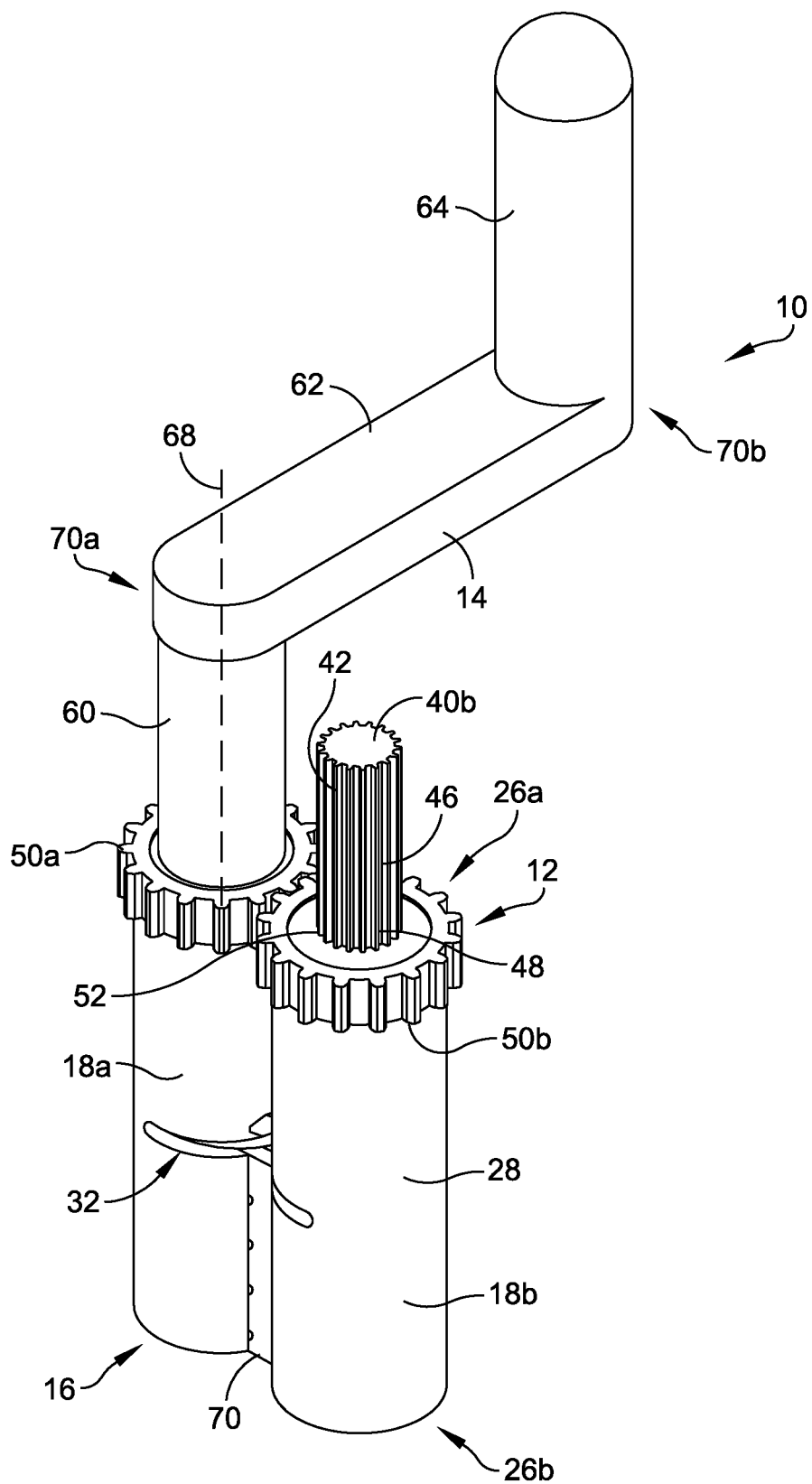
FIG. 1 illustrates an auto-suture device configured for use with an allograft, in accordance with some embodiments.
Figure 3:
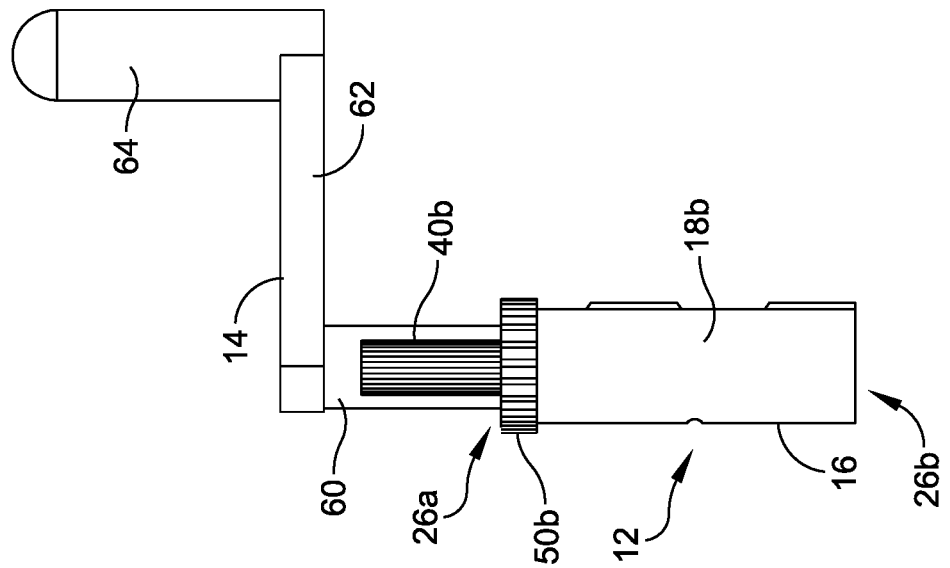
FIG. 3 illustrates a side view of the auto-suture device of FIG. 1, in accordance with some embodiments.
Figure 2:
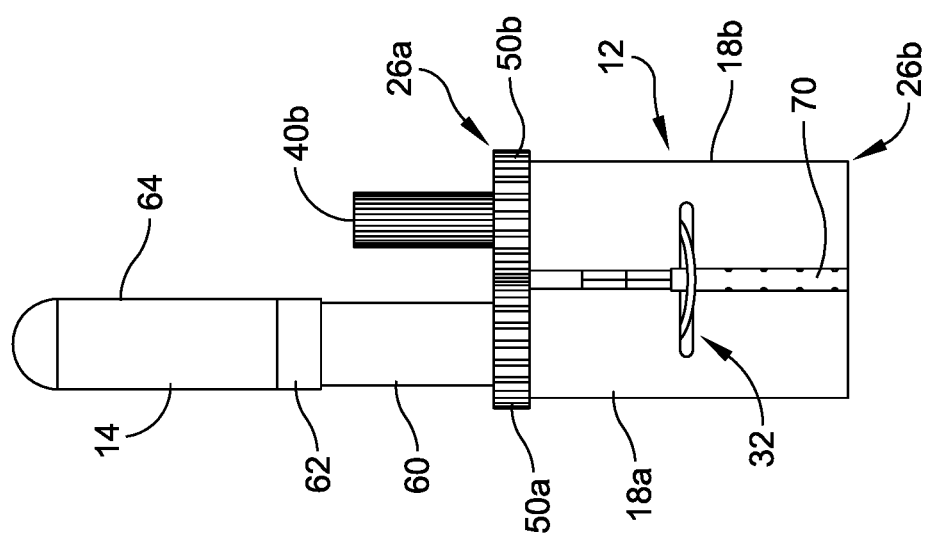
FIG. 2 illustrates a front view of the auto-suture device of FIG. 1, in accordance with some embodiments.
Figure 4:
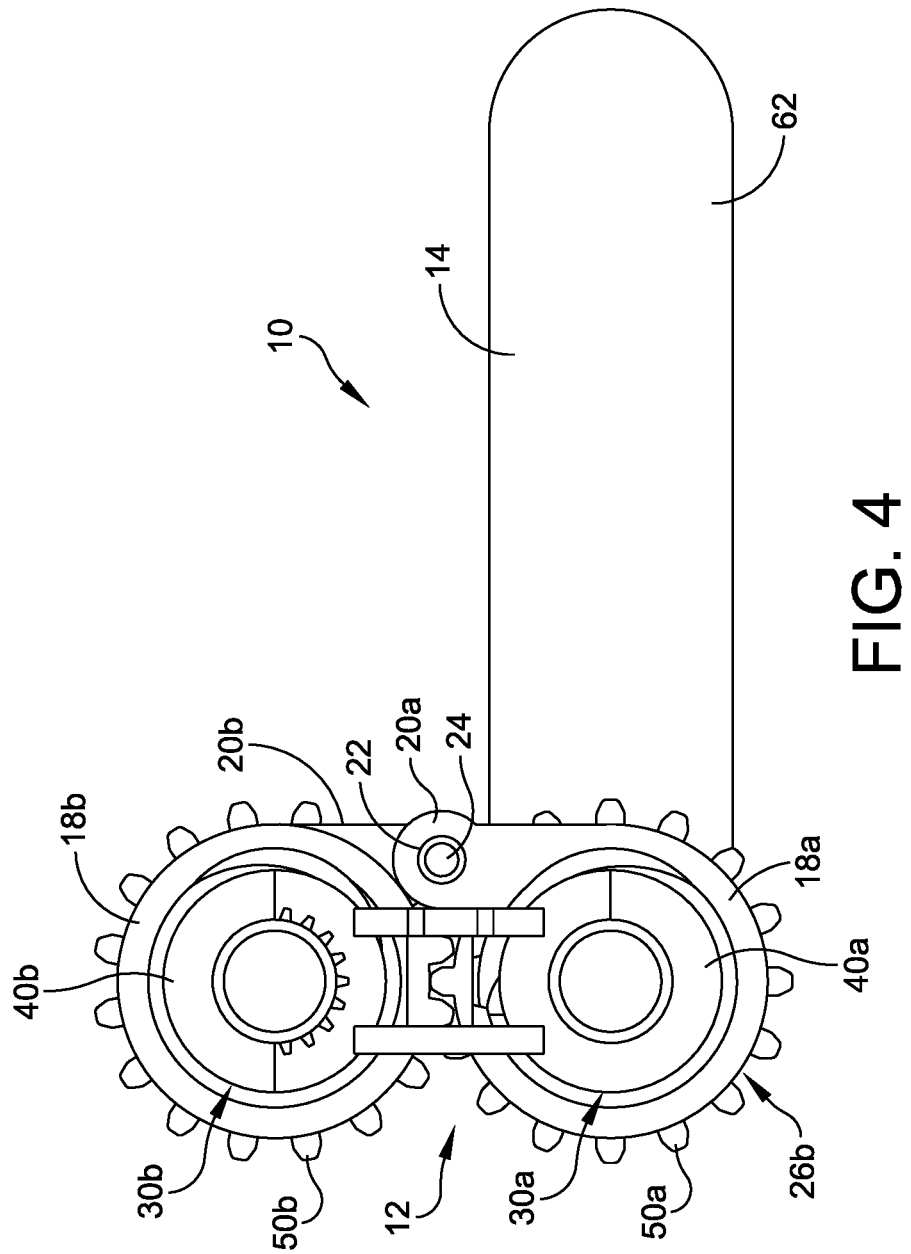
FIG. 4 illustrates a bottom view of the auto-suture device of FIG. 1, in accordance with some embodiments.

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

In various embodiments, an auto-suture device for use in stitching an allograft is disclosed. The auto-suture device includes a spiral drive mechanism configured to receive an allograft therein. The spiral drive mechanism is configured to advance one or more needles through the allograft. The needle is advanced on a path defined by a spiral drive tube of the spiral drive mechanism by a spiral drive element. A suture is coupled to the needle and is advanced through the allograft simultaneous with the needle. In some embodiments, the allograft is compressed within the spiral drive element. A detachable handle may be used to rotate the spiral drive element to advance the needle into the allograft. In some embodiments, a needle capture element is positioned at an end of the spiral drive tube opposite the detachable handle to capture and remove the needle.

FIGS. 1-4 illustrates an auto-suture device 10 configured for use with an allograft, in accordance with some embodiments. The auto-suture device 10 includes a spiral drive mechanism 12 and a detachable handle 14. The spiral drive mechanism 12 includes a housing 16 having one or more spiral drive tubes, such as, for example, a first spiral drive tube 18a and a second spiral drive tube 18b (collectively "spiral drive tubes 18"). In some embodiments, each of the spiral drive tubes 18 defines a hollow cylinder 30a, 30b (collectively "hollow cylinders 30") (see FIGS. 5-7) extending from a first end 26a to a second end 26b and defined by a perimeter wall 28. Each of the spiral drive tubes 18 is sized and configured to receive a spiral drive element 40a, 40b (collectively "spiral drive elements 40") therein. As described in greater detail below with respect to FIGS. 8-9, each of the spiral drive elements 40 includes a drive interface 42 and a needle drive 44. In some embodiments, a surface 46 of the drive interface 42 defines a locking pattern 48 and/or other interface pattern.

In some embodiments, the drive interface 42 of each of the spiral drive elements 40 is sized and configured to couple to a gear cap 50a, 50b (collectively "gear caps 50") coupled to a first end 26a of a respective one of the spiral drive tubes 18. In the illustrated embodiment, each of the gear caps 50 includes an opening 52 defining an internal locking pattern. The internal locking pattern is configured to interface with the locking pattern 48 formed on the longitudinal surface 46 of the drive interface portion 42 to couple rotation of the spiral drive element 40a, 40b and the gear cap 50a, 50b.

In some embodiments, the drive interface 42 of each of the spiral drive elements 40 is sized and configured to interface with the removable handle 14. In the illustrated embodiment, the removable handle 14 includes a drive coupling 60 defining an opening sized and configured to receive the drive interface 42 therein. The opening of the drive coupling 60 may define an internal locking pattern complimentary to the locking pattern 48 of a spiral drive element 18a, 18b and configured to couple the handle 14 to the spiral drive element 40a, 40b.

In some embodiments, the removable handle 14 includes an offset connector 62 and a grip 64. The offset connector 62 extends substantially on a longitudinal axis 66 extending perpendicular to an axis 68 defined by the drive coupling 60. The offset connector 62 is coupled to the drive coupling 60 at a first end 70a and is coupled to the grip 64 at a second end 70b. The grip 64 is sized and configured to be manipulated by a user, such as a surgeon. The surgeon uses the connector 64 to rotate the handle 14 about the longitudinal axis 68 (e.g., the axis 68 defines an axis of rotation for the handle 14). Although embodiments are discussed herein including a handle 14, it will be appreciated that the handle 14 may be replaced with any suitable mechanism for rotating at least one of the spiral drive elements 40, such as, for example, a ratcheting mechanism, an automated mechanism (e.g., a motorized drive element), and/or any other suitable element configured to rotate at least one of the spiral drive elements 40.

In some embodiments, the first gear cap 50a is sized and configured to interface with the second gear cap 50b such that rotation of the first gear cap 50a causes complimentary rotation of the second gear cap 50b. Simultaneous rotation of the gear caps 50 provides simultaneously advancement of the spiral drive elements 40 within a respective one of the spiral drive tubes 18. For example, in the illustrated embodiment, rotation of the handle 14 about the axis 68 causes rotation of the first spiral drive element 40a. Rotation of the first spiral drive element 40a in a first direction advances the spiral drive element 40a within the spiral drive tube 18a and simultaneously causes rotation of a first gear cap 50a due to coupling between the drive interface 42 and the first gear cap 50a. The first gear cap 50a rotates the second gear cap 50b, causing rotation of the second spiral drive element 40b, which advances within the second drive tube 18b. Although embodiments are discussed herein including interfacing gear caps 50a, 50b, it will be appreciated that the auto-suture device 10 may include a drive mechanism configured to independently rotate each of the spiral drive elements 40, either simultaneously and/or sequentially, a drive mechanism configured to rotate only one of the spiral drive elements 40, a spiral drive mechanism including only a single spiral drive element, and/or any other suitable drive mechanism.

In some embodiments, a suture feed channel 32 is defined in each of the spiral drive tubes 18. The suture feed channel 32 defines a slot in the spiral drive tube 18a, 18b positioned a predetermined distance from the second end 26b. The suture feed channel 32 is sized and configured to allow suture to pass into the interior of the spiral drive tube 18a, 18b. In some embodiments, the suture is provided by a suture well, suture roll, and/or other suitable suture source (not shown). The suture source may be coupled to an exterior surface and/or portion of the auto-suture device 10, such as an exterior surface of one or more of the spiral drive tubes, and/or may be positioned remotely from the auto-suture device 10.

Figure 6:
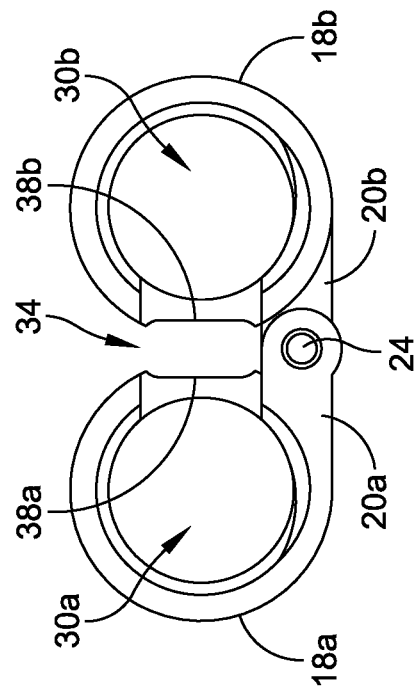
FIG. 6 illustrates the first spiral drive tube and the second spiral drive tube of FIG. 5 in a second, closed position, in accordance with some embodiments.
Figure 5:
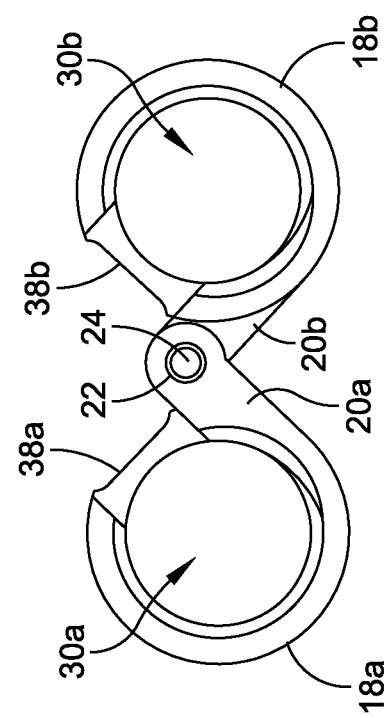
FIG. 5 illustrates a bottom view of a first spiral drive tube and a second spiral drive tube coupled in a pivoting arrangement and configured in a first, open position, in accordance with some embodiments.

In some embodiments, the spiral drive tubes 18 are releasably and/or moveably coupled, such as, for example, in a pivoting arrangement (FIGS. 1-20), a sliding arrangement (FIGS. 21-23), and/or any other suitable arrangement. As illustrated in FIGS. 5-6, in some embodiments, the first spiral drive tube 18a is coupled in a pivoting arrangement to the second spiral drive tube 18b. The first spiral drive tube 18a defines a first pivot element 20a and the second spiral drive tube 18b defines a second pivot element 20b. The first pivot element 20a and the second pivot element 20b each define a pivot pin hole 22 sized and configured to receive a pivot pin 24 therein. The first pivot element 20a is positioned in a partially overlapping configuration with the second pivot element 20b and the pivot pin 24 is inserted through the pivot pin holes 22 to couple the first spiral drive tube 18a to the second spiral drive tube 18b in a pivoting arrangement.

FIG. 5 illustrates the spiral drive tubes 18 in a first (e.g., open or pivoted) configuration in which the first spiral drive tube 18a and the second spiral drive tube 18b are pivoted about the pivot pin 24 to increase the distance between a first sidewall 38a and a second sidewall 38b of respective first spiral drive tube 18a and second spiral drive tube 18b. FIG. 6 illustrates the spiral drive tubes 18 in a second (e.g., closed) configuration in which the first sidewall 38a and the second sidewall 38b are parallel. The spiral drive tubes 18 may be transitioned from the closed position (FIG. 6) to the open position (FIG. 5) to receive an allograft and subsequently transitioned from the open position (FIG. 5) to the closed position (FIG. 6) to capture or maintain the allograft between the spiral drive tubes 18. Although specific embodiments are discussed herein, it will be appreciated that any suitable mechanism can be used to couple the first spiral drive tube 18a to the second spiral drive tube 18b, such as, for example, any suitable pivoting element, slide element, release element, latch element, etc.

Figure 7:
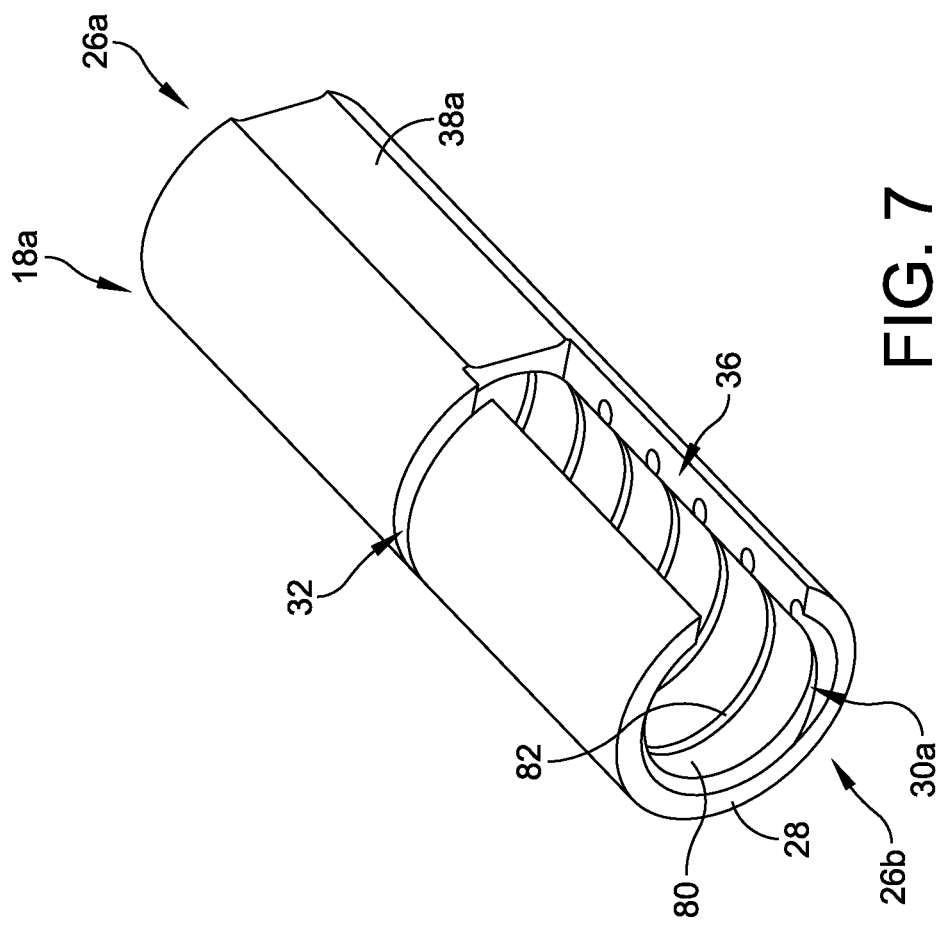
FIG. 7 illustrated a spiral drive tube having an allograft channel, suture feed channel, sidewall, and internal spiral drive travel path, in accordance with some embodiments.

FIG. 7 illustrates a spiral drive tube 18a including an allograft channel 36 and a flat sidewall 38a, in accordance with some embodiments. The allograft channel 36 extends from the second end 26b of the spiral drive tube 18a a predetermined distance into the perimeter wall 28. In some embodiments, the allograft channel 36 extends from the second end 26 to the suture feed channel 32, although it will be appreciated that the allograft channel 36 may extend beyond and/or may terminate prior to intersecting the suture feed channel 32. The allograft channel 36 is sized and configured to receive a portion of an allograft therein, such as, for example, a compressed distal portion of an allograft.

In some embodiments, the sidewall 38a extends from the first end 26a of the spiral drive tube 18a a predetermined distance parallel to a longitudinal axis of the spiral drive tube 19a. The sidewall 38a is sized and configured to interface with a portion of an allograft. As illustrated in FIG. 6, a first sidewall 38a and a second sidewall 38b may cooperatively define a retention channel 34 for receiving and retaining a portion of an allograft therein. In some embodiments, the sidewalls 38a, 38b include a curved profile complimentary to a curvature of an allograft to be positioned between the sidewalls 383a, 38b. Although embodiments are discussed herein including cylindrical spiral drive tubes 18 having a single sidewall portion 38a, 38b, it will be appreciated that the spiral drive tubes 18 may include any suitable shape, such as, for example, a rectangular shape defining four flat sidewalls, a cylindrical shape omitting the flat sidewall, and/or any other suitable shape.

In some embodiments, an interior surface 80 of the spiral drive tube 18a defines a spiral drive travel path 82. The spiral drive travel path 82 includes a channel formed in the interior surface 80 sized and configured to match a pitch and radius of the needle drive 44 of a spiral drive element 40. In some embodiments, the spiral drive path 82 includes a discontinuous channel extending through the portion of the spiral drive tube 18a defining the allograft channel 36. The spiral drive travel path 82 guides insertions of a needle through an allograft positioned and retained between the spiral drive tubes 18, as discussed in greater detail below.

Figure 8:
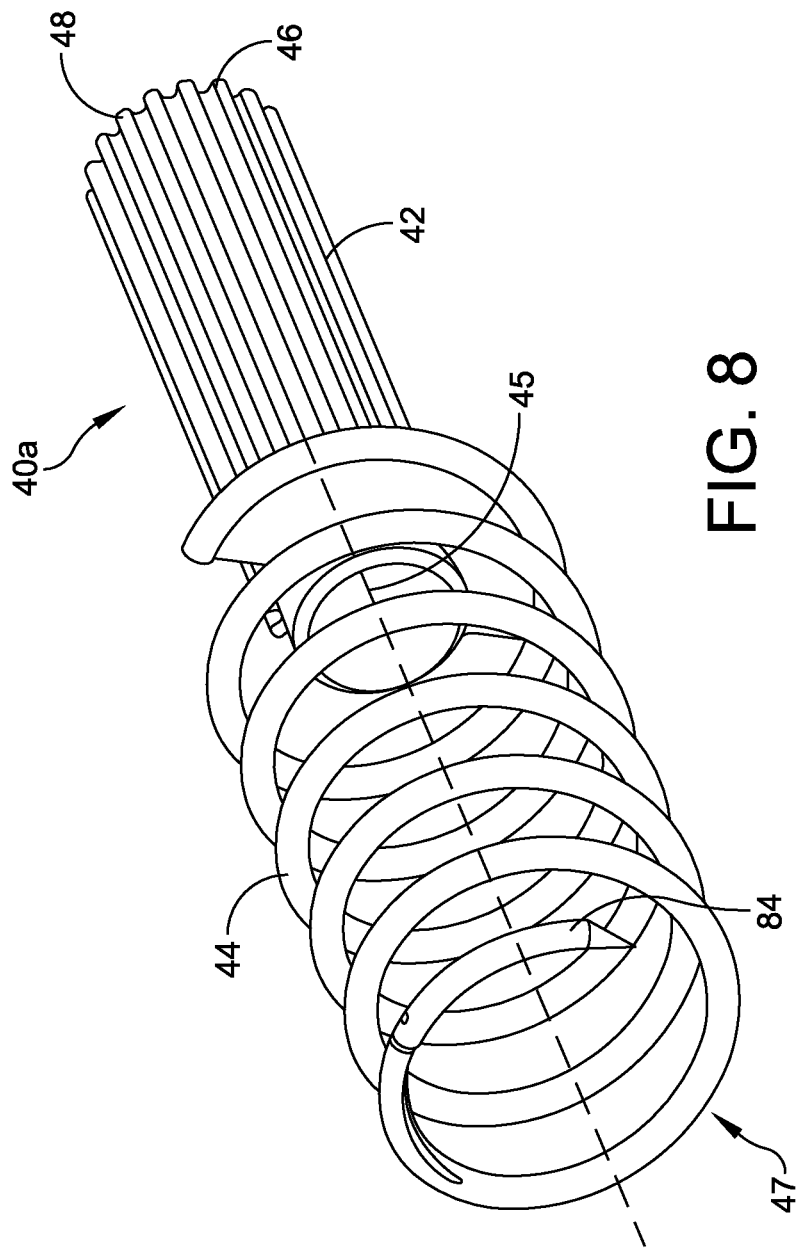
FIG. 8 illustrates a spiral drive element in accordance with some embodiments.

FIG. 8 illustrates a spiral drive element 40a having a drive interface 42 and a needle drive 44, in accordance with some embodiments. The drive interface 42 defines a cylinder extending substantially along a longitudinal axis 45. The outer surface 46 of the drive interface 42 defines a locking pattern 48. As discussed above, the locking pattern 48 is configured to couple the interface 42 to a gear cap 50a, a handle 14, and/or any other suitable drive mechanism. Although a single locking pattern 48 is illustrated, it will be appreciated that the drive interface 42 may define any number of locking patterns, such as, for example, a first locking pattern configured to couple the drive interface 42 to a gear cap 50a and a second locking pattern configured to couple the drive interface 42 to a handle 14.

In some embodiments, the needle drive 44 defines a helix extending from the drive interface 42. The pitch and diameter of the needle drive 44 is configured to match the pitch and diameter of the spiral drive travel path 82 defined in the interior surface 80 of a spiral drive tube 18a, 18b. A needle 84 is coupled to a distal end 47 of the needle drive 44. The needle 84 may be fixedly and/or releasably coupled to the distal end 47 of the tube interface portion 44, as discussed in greater detail below.

Figure 9:
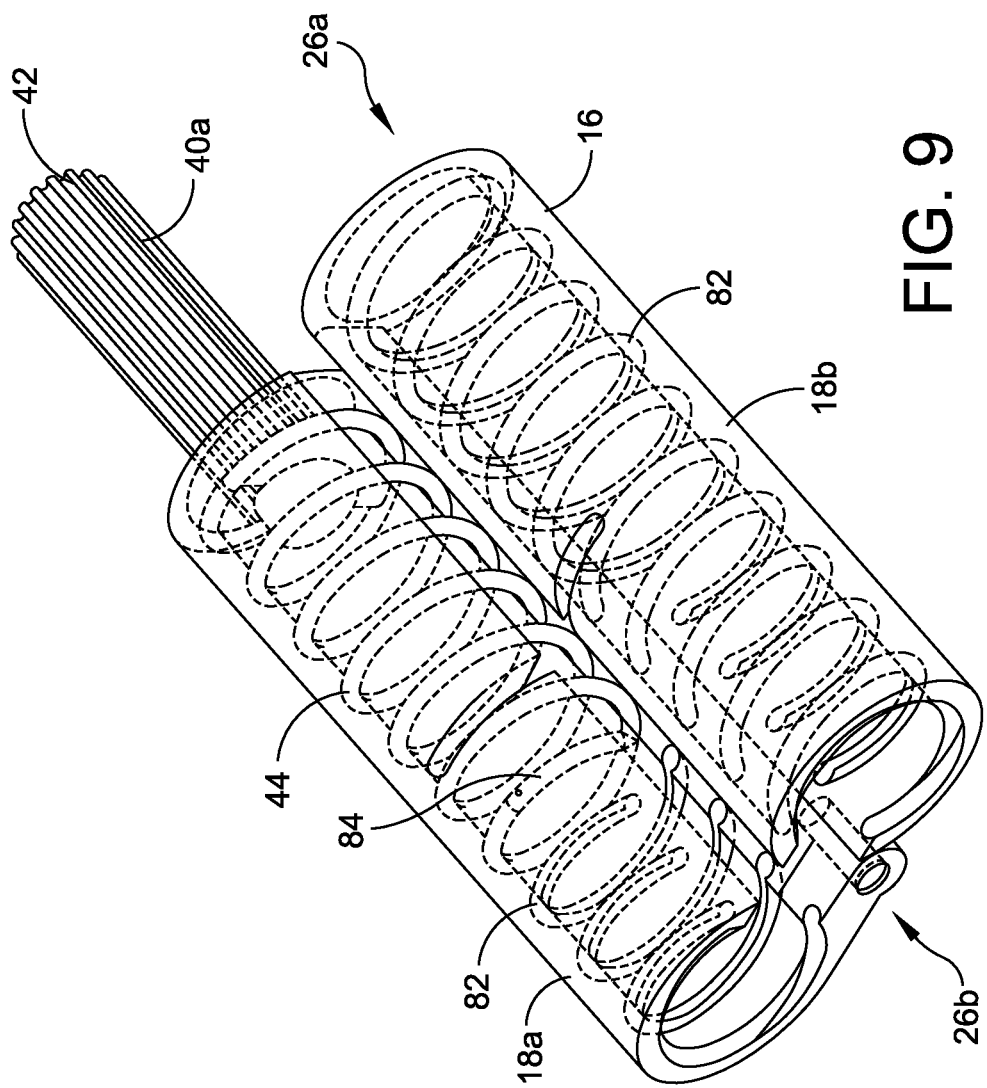
FIG. 9 illustrates the spiral drive element of FIG. 8 partially inserted into a first spiral drive tube of a spiral drive body, in accordance with some embodiments.

As illustrated in FIG. 9, the needle drive 44 of the spiral drive element 40a may be coupled to a spiral drive travel path 82 defined by the spiral drive tube 18a, in accordance with some embodiments. Rotation of the spiral drive element 40a, for example, due to rotation of a handle 14 coupled to a drive interface 42, causes the needle drive 44 to rotate and advance within the spiral drive travel path 82. Rotation of the spiral drive element 40a in a first direction causes the needle drive 44 to move distally and rotation of the spiral drive element 40b in a second, opposite direction causes the needle drive 44 to move proximally.

Figure 10:
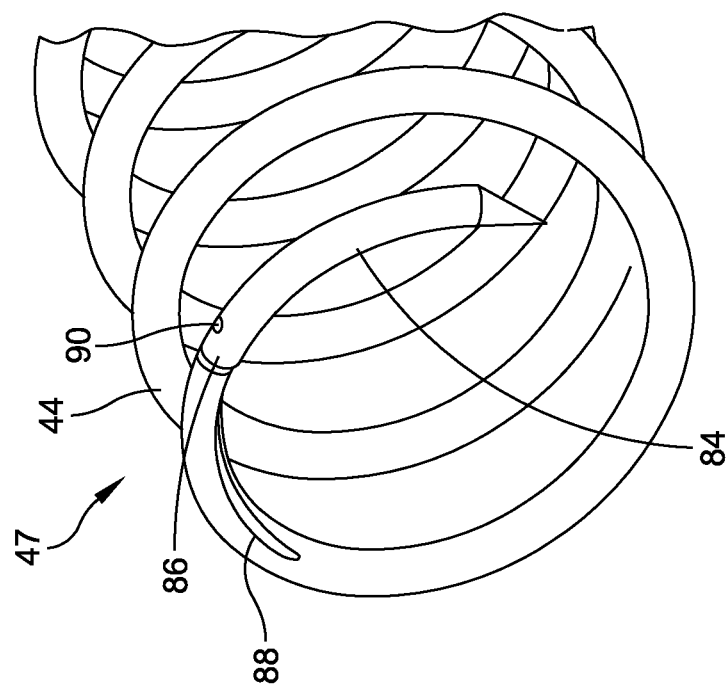
FIG. 10 illustrates a distal end of the spiral drive element of FIG. 8 having a needle coupled thereto, in accordance with some embodiments.

FIG. 10 illustrates an expanded view of a distal end 47 of the needle drive 44 including a needle 84 releasably coupled thereto, in accordance with some embodiments. The needle 84 may be releasably coupled to the needle drive 44 using any suitable mechanism. For example, in the illustrated embodiment, a coupling portion 86 of the needle 84 is slideably received within a needle channel 88 defined by the distal end 47 of the needle drive 44, although it will be appreciated that any suitable coupling mechanism may be used, such as, for example, a friction coupling mechanism, a locking mechanism, an adhesive, and/or any other suitable coupling mechanism. In some embodiments, the needle 84 is formed integrally with the needle drive 44.

In some embodiments, the needle 84 includes a suture coupling hole 90 sized and configured to receive a suture (not shown) therethrough. The suture may be coupled to the needle 84, for example, by tying a knot in the suture after inserting the suture through the coupling hole 90. In operation, and as described in greater detail below, the needle 84 is advanced through an allograft by rotating the spiral drive element 40a. The needle 84 similarly advances the suture through the allograft. In some embodiments, the spiral drive element 40a may be advanced to a distal position configured to position the needle 84 and/or the needle drive 44 outside of the spiral drive tube 18a to allow the needle 84 to be separated from the needle drive 44, as discussed in greater detail below.

Figure 11:
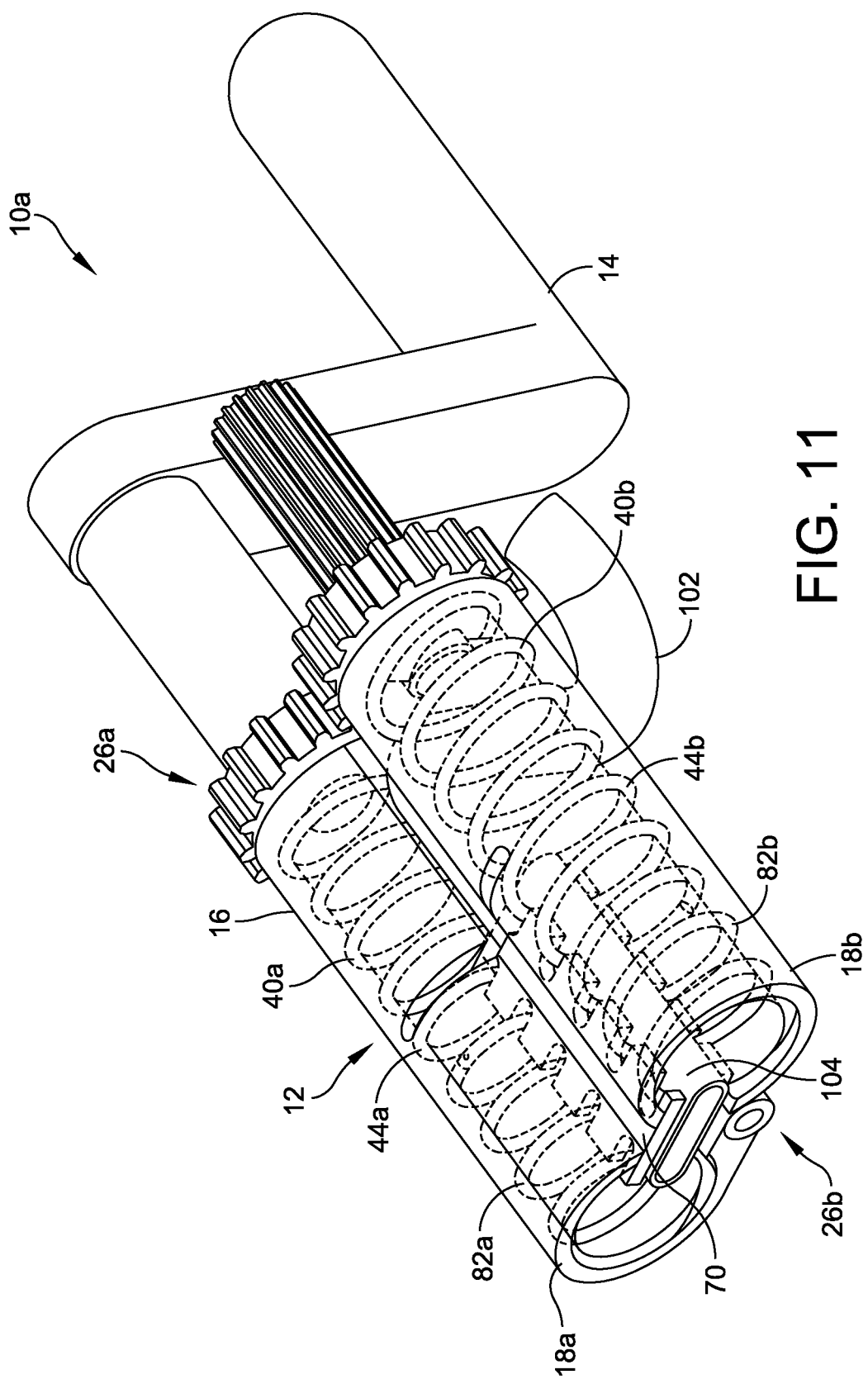
FIG. 11 illustrates an auto-suture device having an allograft inserted between a first spiral drive tube and a second spiral drive tube of a spiral drive mechanism, in accordance with some embodiments.
Figure 12:
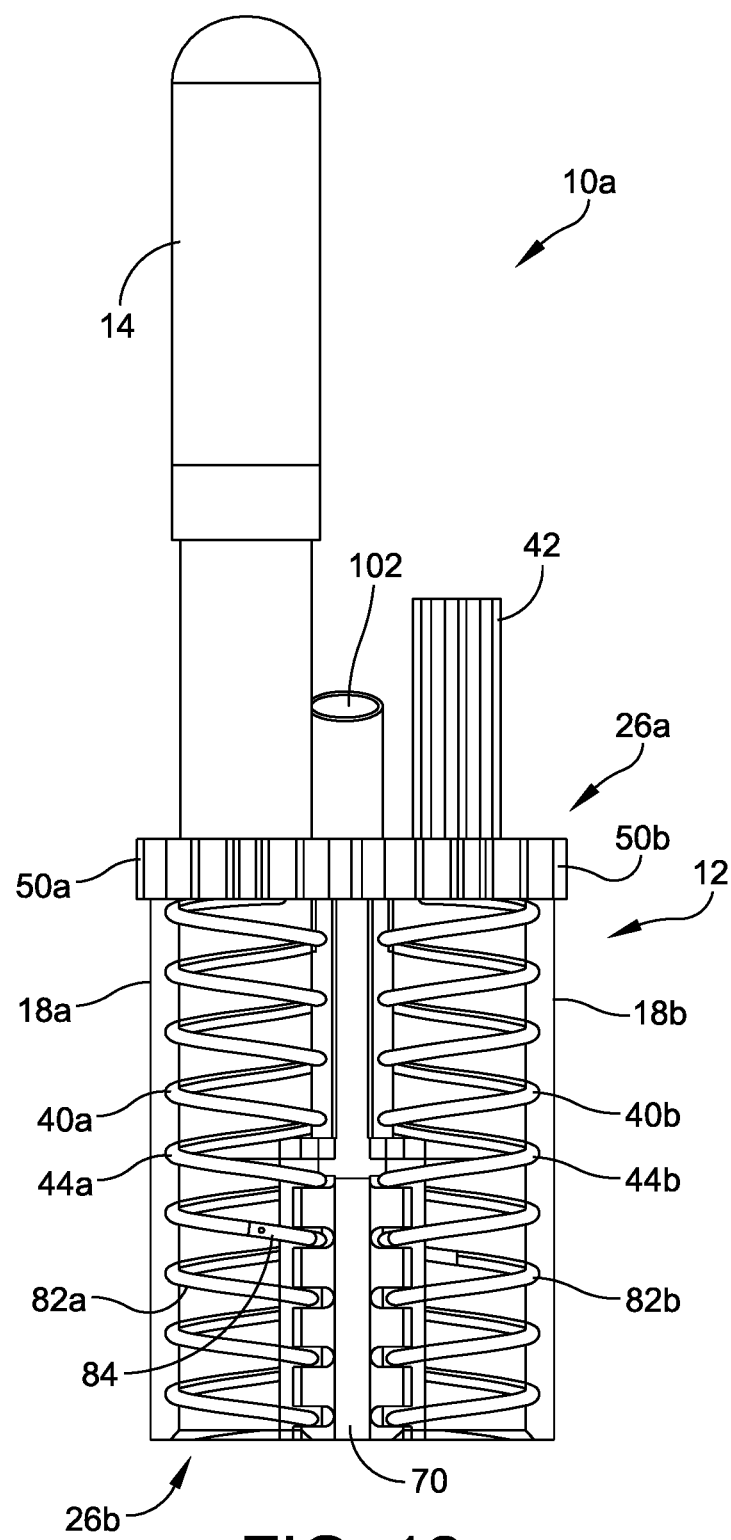
FIG. 12 illustrates a front view of the auto-suture device of FIG. 11, in accordance with some embodiments.
Figure 13:
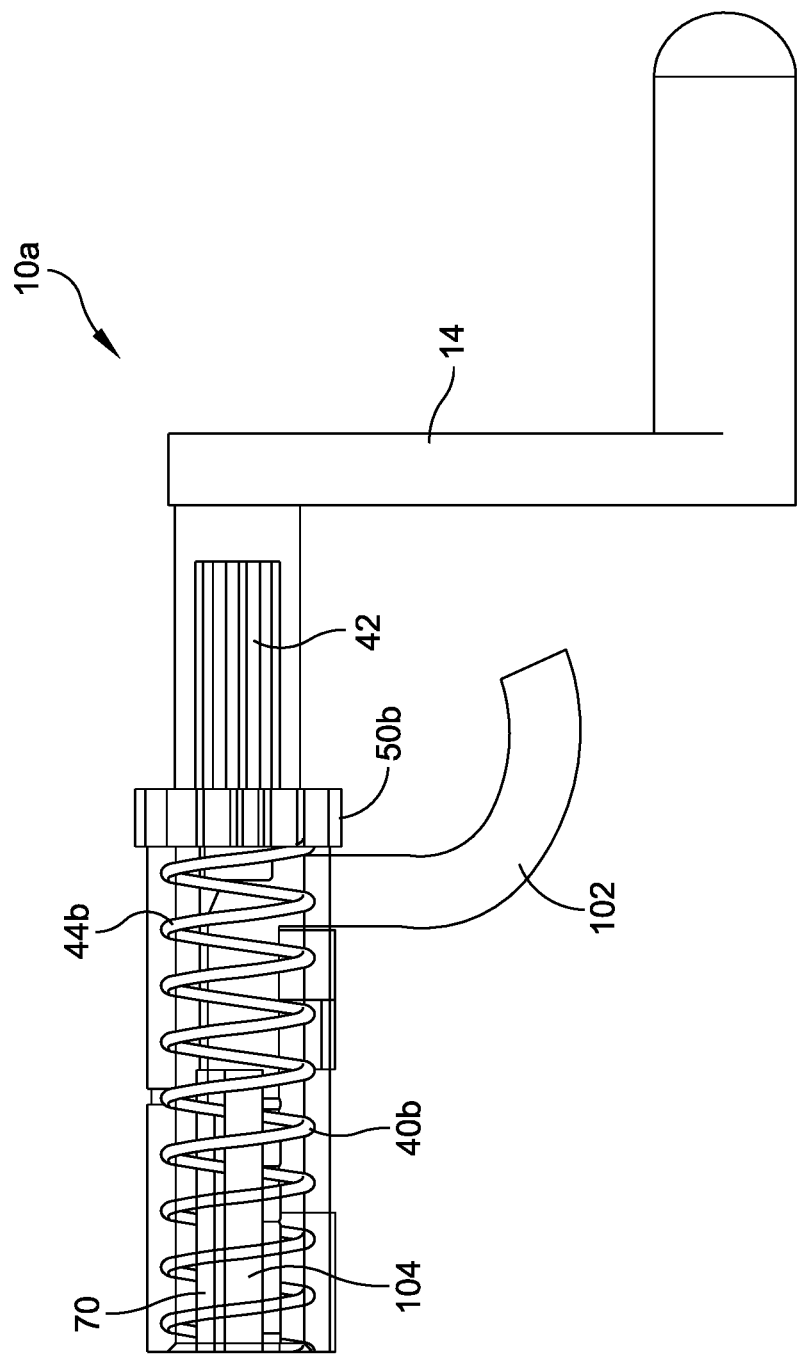
FIG. 13 illustrates a side view of the auto-suture device of FIG. 11, in accordance with some embodiments.

FIGS. 11-18 illustrate one embodiment of an auto-suture device 10a having an allograft 102 coupled thereto, in accordance with some embodiments. The auto-suture device 10a is similar to the auto-suture device 10 discussed above in conjunction with FIGS. 1-10, and similar description is not repeated herein. As illustrated in FIG. 11, an allograft 102 is fed into a spiral drive portion 12a of the auto-suture device 10a, for example, between a first spiral drive tube 18a and a second spiral drive tube 18b. In some embodiments, the spiral drive tubes 18 may be pivoted from an open position configured to receive an allograft 102 therebetween to a closed position to maintain the allograft 102 in a fixed position with respect to the auto-suture device 10a, for example, as illustrated in FIGS. 5-6 and discussed above.

In some embodiments, the allograft 102 is fed through a posterior (or rear) portion of the spiral drive element 12a, although it will be appreciated that auto-suture device 10a may be configured to provide for passage of the allograft 102 from an anterior (or front) portion of the spiral drive element 12a. A portion of the allograft 102 is positioned to interface with a movable compression plate 70 when the spiral drive element is closed (e.g., when the first spiral drive tube 18a and the second spiral drive tube 18b are rotated from an open position as illustrated in FIG. 6 to a closed position as illustrated in FIG. 5). The moveable compression plate 70 is sized and configured to compress a portion of the allograft 102 prior to insertion of a needle 84 into the allograft 102.

Figure 14:
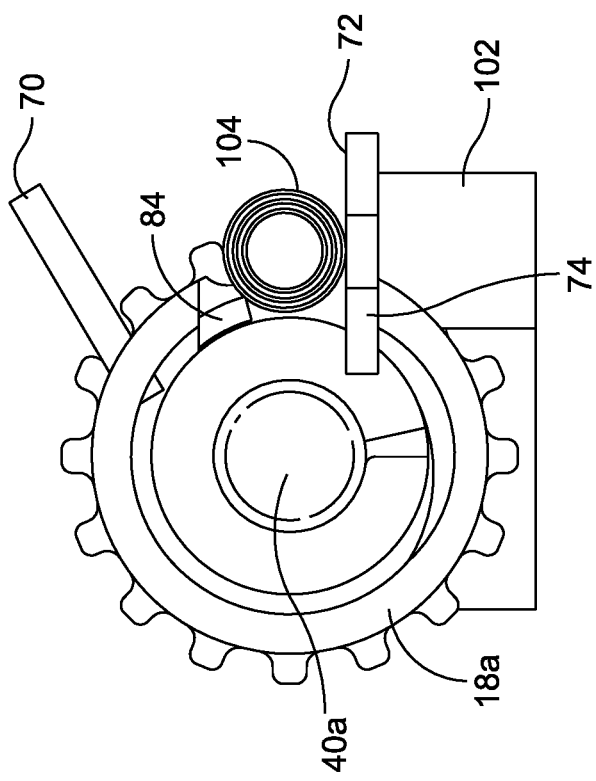
FIG. 14 illustrates a bottom view of a spiral drive tube having a moveable compression plate coupled thereto and located in a first position, in accordance with some embodiments.

FIG. 14 illustrates a first spiral drive tube 18a including a compression plate 70 coupled thereto, in accordance with some embodiments. An allograft 102 is positioned at least partially against a surface of the spiral drive tube 18a, such as a fixed compression surface 72. The fixed compression surface 72 may be a surface defined by the first spiral drive tube 18a and/or a surface defined by an interface between the first spiral drive tube 18a and one or more other structures, such as, for example, a second spiral drive tube 18b (not shown). In the illustrated embodiment, the fixed compression surface 72 is defined by a compression block 74 coupled to the first spiral drive tube 18a in a fixed position with respect to a pivot element 20a of the first spiral drive tube 18a (see FIG. 16).

Figure 15:
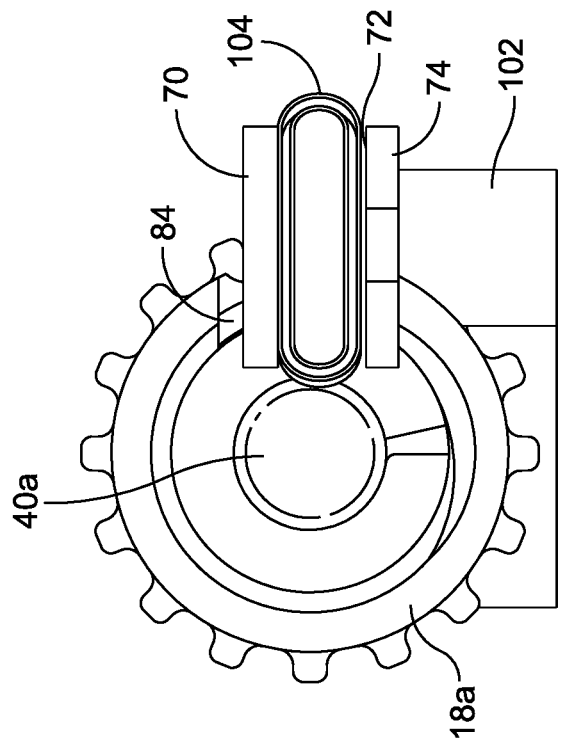
FIG. 15 illustrates the spiral drive tube of FIG. 14 having the moveable compression plate in a second position configured to compress an allograft, in accordance with some embodiments.

In use, the movable compression plate 70 is rotated from a first position in which the allograft 102 is not compressed (illustrated in FIG. 14) to a second position in which a distal portion 104 of the allograft 102 is compressed between the movable compression plate 70 and the fixed compression surface 72 (illustrated in FIG. 15). The movable compression plate 70 compresses the distal portion 104 of the allograft 102 such that the allograft 102 is elongated on an axis perpendicular to the axis of compression. The allograft 102 is elongated and maintained in a fixed position by the movable compression plate 70 such that a needle 84 coupled to a spiral drive element 40a penetrates a distal portion 104 of the allograft 102 when the spiral drive element 40a is rotated and advanced within the spiral drive tube 18a.

Figure 16:
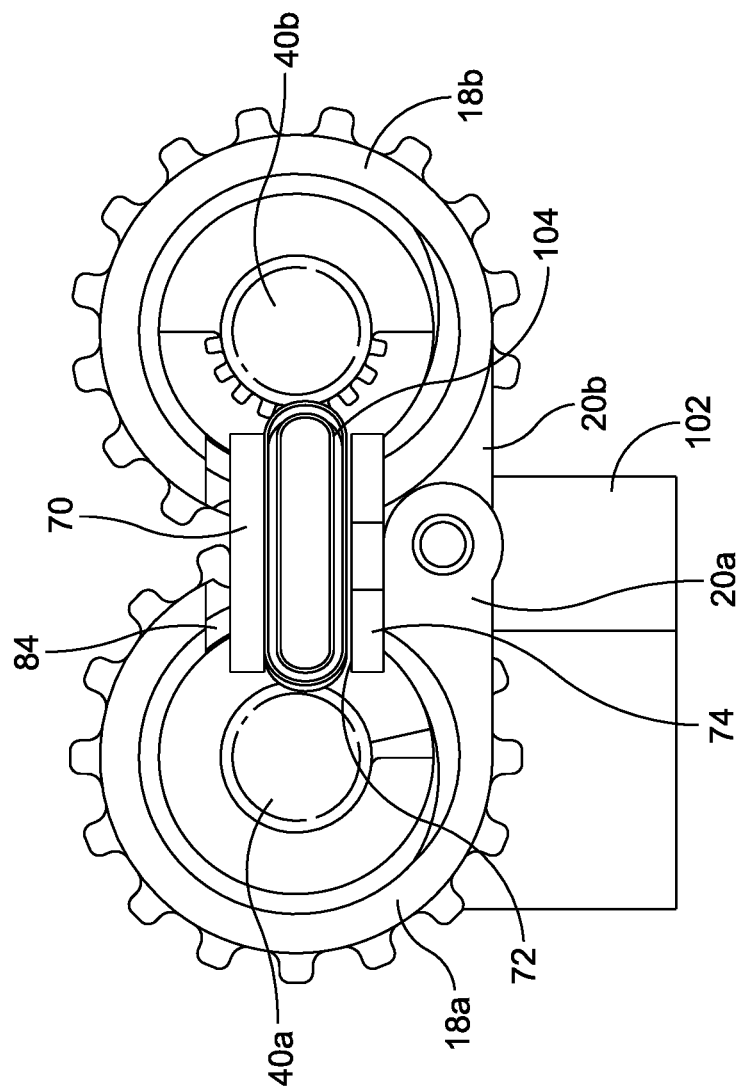
FIG. 16 illustrates a bottom view of a spiral drive mechanism including the spiral drive tube and movable compression plate of FIG. 14, in accordance with some embodiments.

As illustrated in FIG. 16, the movable compression plate 70 and/or the fixed compression block 74 may be configured to extend from a first spiral drive tube 18a to a second spiral drive tube 18b when the spiral drive element 12 is in a closed position. The moveable compression plate 70 and/or the fixed compression block 74 may be coupled to one of the spiral drive tubes 18a, 18b and/or an underlying structure such that rotation of the spiral drive element 12 from a closed position (as illustrated in FIG. 16) to an open position causes the moveable compression plate 70 to rotate to an open position (as illustrated in FIG. 14) to release the distal portion 104 of the allograft 102. Although embodiments are illustrated having a moveable compression plate 70 coupled to the first spiral drive tube 18a, it will be appreciated that the compression plate may be coupled to any suitable portion of the auto-suture device 10a.

Figure 17:
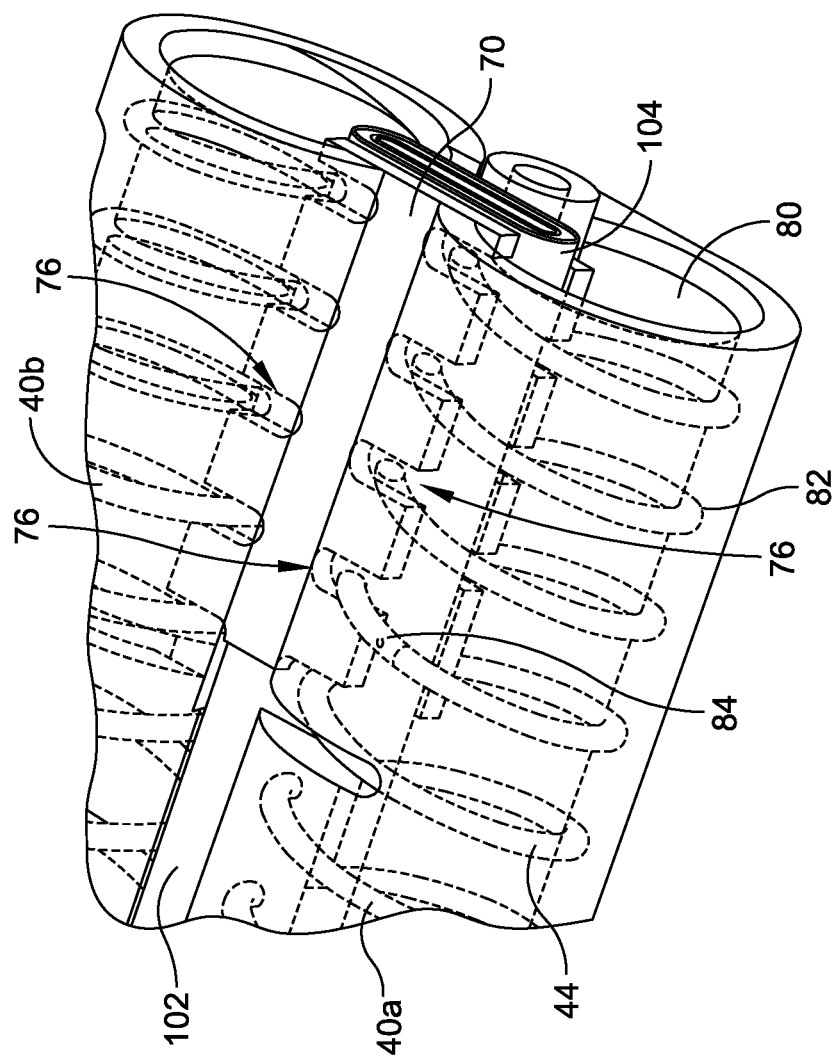
FIG. 17 illustrates a distal portion of the spiral drive mechanism of FIG. 16 after a needle is partially driven through an allograft, in accordance with some embodiments.

As illustrated in FIG. 17, in some embodiments, the movable compression plate 70 includes a plurality of cutouts 76 (e.g., divots, scallops, insets, etc.) sized and configured to align with a travel path of a needle 84 and corresponding spiral drive element 40a during advancement of the spiral drive element 40a within the spiral drive tube 18a. For example, in some embodiments, the cutouts 76 are aligned with the travel path 82 of the spiral drive section 44 of the spiral drive element 40a defined by the inner surface 80 of the spiral drive tube 18a. Although embodiments are illustrated including cutouts 76, it will be appreciated that the compression plate 70 may have a width that positions the compression plate 70 outside of the travel path of the spiral drive portion 44, may have a material configured to allow passage of a needle 84 through the material, and/or may otherwise be configured to allow the needle 84 to pass into the distal portion 104 of the allograft 102.

Figure 18:
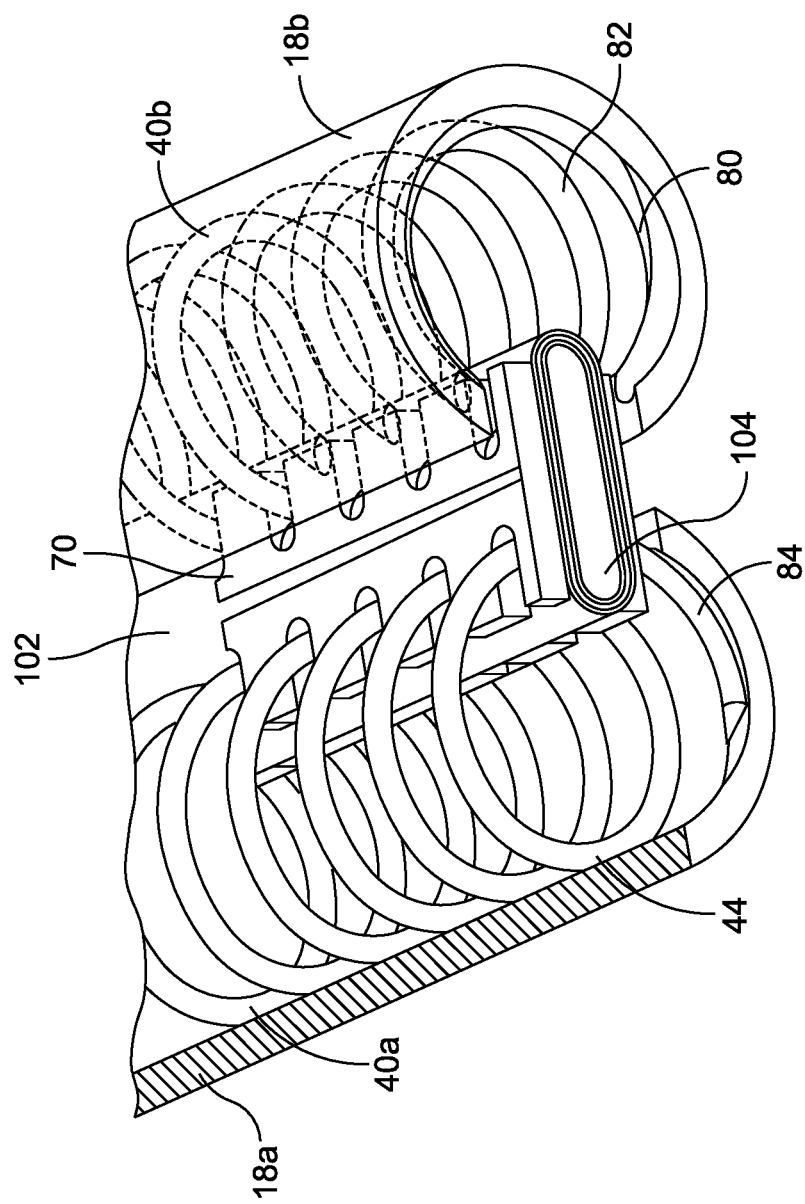
FIG. 18 illustrates the distal portion of the spiral drive mechanism of FIG. 16 after a needle has been advanced multiple times through an allograft, in accordance with some embodiments.

After compressing the distal portion 104 of the allograft 102 between the movable compression plate 70 and the fixed compression surface 72, spiral drive element 40 may be rotated to advance one or more needles 84 into the allograft 102. For example, as shown in FIG. 18, a first spiral drive element 40a having a first needle 84 coupled thereto has been advanced to a distal end of the spiral drive tube 18a. The needle 84 penetrates the distal portion 104 of the allograft 102 multiple times during advancement of the spiral drive element 18a. For example, in the illustrated embodiment, the needle 84 as penetrated the allograft 102 five times, although it will be appreciated that the pitch and/or diameter of the spiral drive element 18a may be adjusted to increase and/or decrease the number of interactions between the needle 84 and the allograft 102.

In some embodiments, a suture (not shown) is coupled to each needle 84 and is carried through the allograft 102 each time the needle 84 penetrates the allograft 102. The suture may be configured to provide coupling of the allograft to one or more additional anatomical structures. The suture may be knotted and/or otherwise coupled to the allograft 102 at a proximal end and/or a distal end. In some embodiments, the suture is provided by a suture reservoir (or well) (not shown) coupled to an outer surface of the auto-suture device 10a.

In some embodiments, a first needle is coupled to a first spiral drive element 40a and a second needle is coupled to a second spiral drive element 40b. The first needle is further coupled to at least a first suture strand and the second needle is coupled to at least a second suture strand. The first spiral drive element 40a may be coupled to a handle 14, which may be rotated about an axis of rotation. As discussed above, in some embodiments, rotation of the handle 14 causes the first spiral drive element 40a and the second spiral drive element 40b to simultaneously rotate and advance within respective spiral drive tubes 18a, 18b, driving the first needle and the second needle through parallel paths on opposite sides of the allograft 102.

Figure 19:
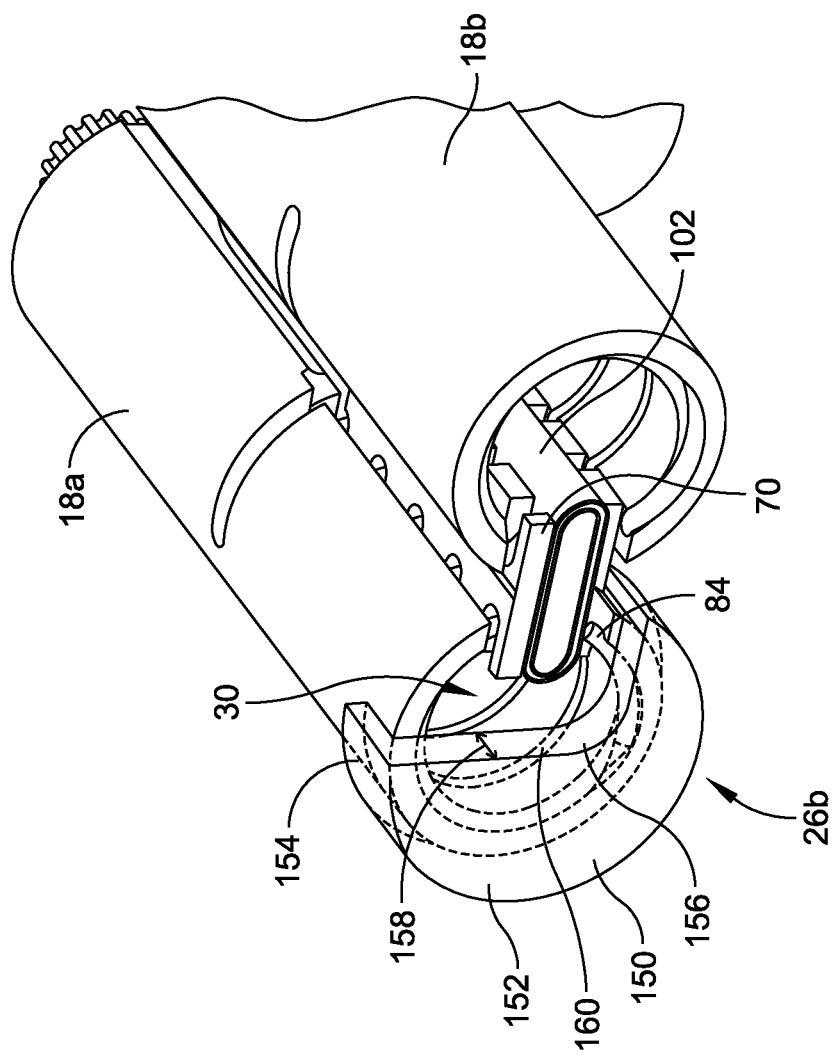
FIG. 19 illustrates a spiral drive mechanism having a needle capture element coupled to a second end of a spiral drive tube, in accordance with some embodiments.
Figure 20:
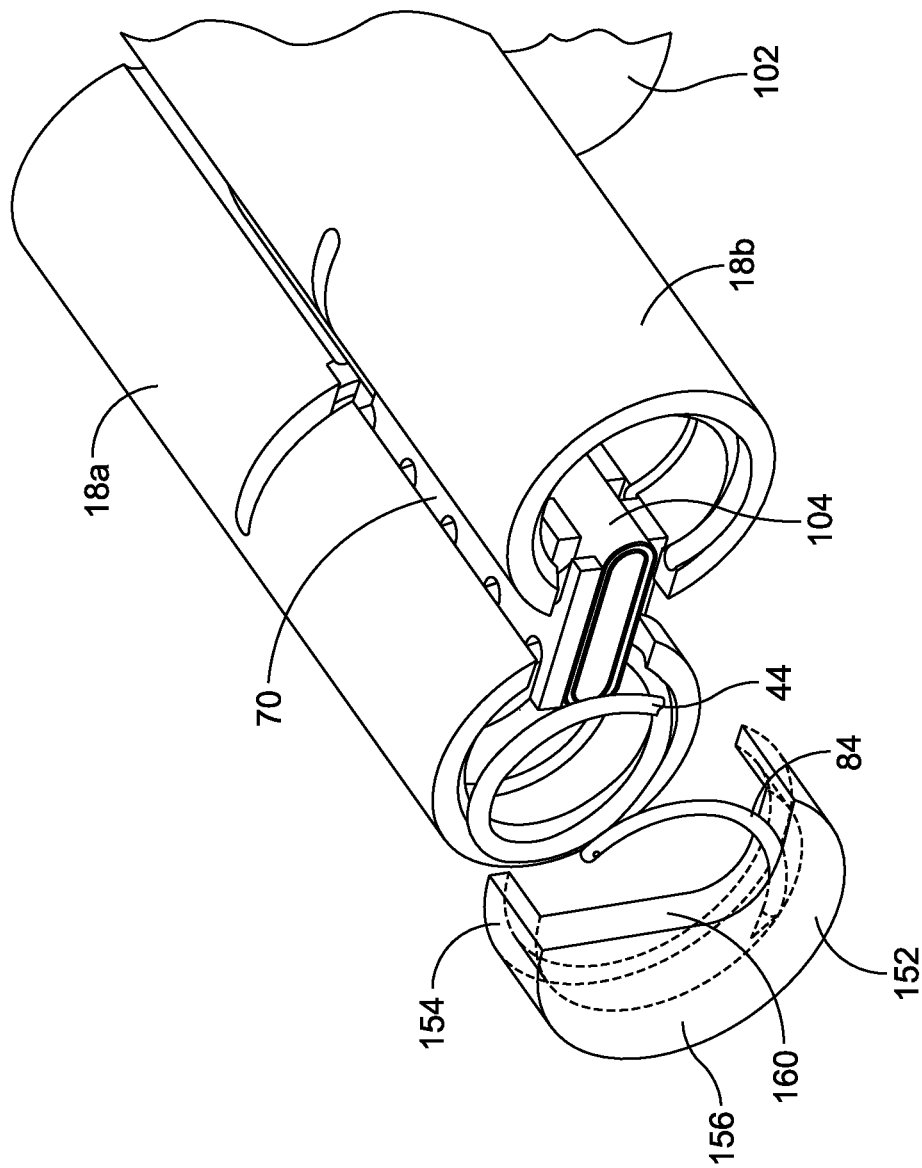
FIG. 20 illustrates the needle capture element removed from the spiral drive mechanism after capturing a suture needle, in accordance with some embodiments.

In some embodiments, a needle capture element may be disposed at and/or coupled to a distal end 26b of a spiral drive tube 18a. For example, FIGS. 19-20 illustrate an embodiment of a needle capture element 150 including a capture cap 152. The capture cap 152 is sized and configured to couple to a distal end 26b of a spiral drive tube 18a. The capture cap 152 may partially and/or completely cover the interior channel 30 defined by the spiral drive tube 18a. In some embodiments, the capture cap 152 includes a material configured to be pierced by the needle 84 such that the needle 84 is retained by the capture cap 152 (as shown in FIG. 20). For example, the capture cap 152 may include any suitable material such as silicone, plastic, rubber, etc.

In some embodiments, the capture cap 152 includes a coupling portion 154 and a needle capture portion 156. The coupling portion 154 is sized and configured to couple the capture cap 152 to a distal end 26b of a spiral drive tube 18a. In some embodiments, the coupling portion 154 includes a partial cylinder having an inside diameter sized and configured to be friction-fit over the outer diameter of the distal end 26b of the spiral drive tube 18a. In other embodiments, the coupling portion 154 may include any suitable coupling element, such as, for example, a friction-fit element, a threaded coupling element, a locking coupling element, etc.

In some embodiments, the needle capture portion 156 includes a material having a predetermined thickness 158. The predetermined thickness 158 may be greater than and/or equal to the diameter of a needle 84 such that the needle capture portion 156 may receive a portion of the needle 84 therein such that the entire diameter of the needle is contained within the material. In some embodiments, the needle capture portion 156 includes an interface surface 160 positioned at an angle and/or otherwise configured to facilitate piercing of the needle capture portion 156 by the needle 84.

In some embodiments, the capture cap 152 includes an outer profile configured to match an outer profile of the spiral drive tubes 18. For example, in the illustrated embodiment, each of the spiral drive tubes 18 include a cylindrical or circular outer profile (or cross-section) and the capture cap 152 includes a similar cylindrical or circular outer profile (or cross-section). Although embodiments of the capture cap 152 are illustrated as having a similar outer profile as compared to the spiral drive tubes 18, it will be appreciated that the capture cap 152 may have any suitable outer profile, such as, for example, a regular geometric shape, an irregular shape, etc. that may or may not match the outer profile of a corresponding spiral drive tube 18a, 18b.

In some embodiments, the capture cap 152 is releasably coupled to the spiral drive tube 18a. As illustrated in FIG. 20, after the needle 84 has been driven into and retained by the capture cap 152, the needle 84 may be disconnected from the needle drive 44 and the capture cap 152 may be removed from the spiral drive tube 18a. The capture cap 152 may be manually removed by a user and/or automatically removed by advancement of the spiral drive element 40a beyond a distal edge of the spiral drive tube 18a. A user, such as a surgeon, may use the capture cap 152 and the retained needle 84 to tie one or more knots in a suture coupled to the needle 84 and/or may discard the capture cap 152 and the retained needle 84 as a single unit. Although embodiments are illustrated including a capture cap 152, it will be appreciated that the needle capture element 150 can include any suitable capture element.

Figure 21:
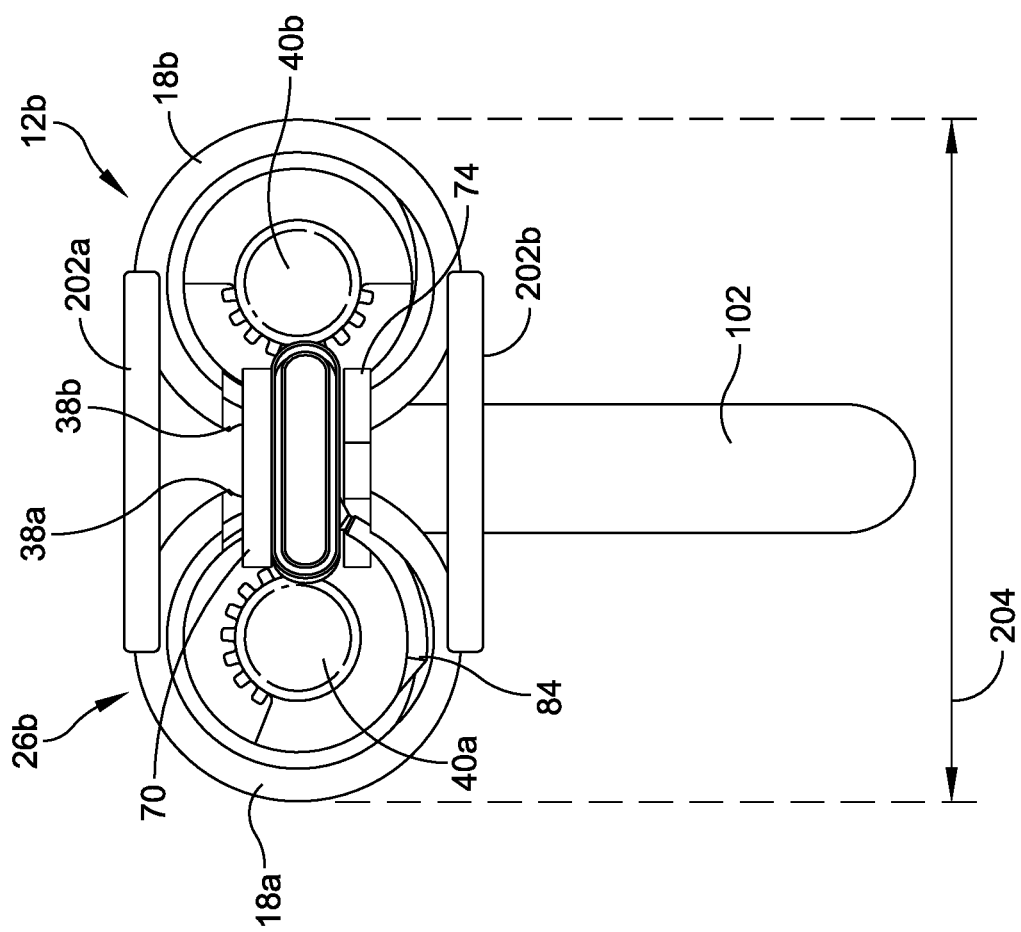
FIG. 21 illustrates an auto-suture device including a spiral drive mechanism having an adjustable spacing, in accordance with some embodiments.

FIG. 21 illustrates a spiral drive mechanism 12b having an adjustable spacing, in accordance with some embodiments. The spiral drive mechanism 12b is similar to the spiral drive mechanisms 12, 12a discussed above, and similar description is not repeated herein. The spiral drive mechanism 12b includes a first spiral drive tube 18a coupled to a second spiral drive tube 18b by a first slideable coupling element 202a coupled to a first side 204 of the spiral drive mechanism 12b and a second slideable coupling element 202b coupled to a second side 206 of the spiral drive mechanism 12b (collectively "slideable coupling elements 202"). The slidable coupling elements 202 are configured to adjustably couple the first spiral drive tube 18a to the second spiral drive tube 18b, as described in greater detail below.

In some embodiments, each of the slideable coupling elements 202 may be slideably coupled to each of the spiral drive tubes 18. For example, in some embodiments, each of the spiral drive tubes 18 may include one or more slots or other openings (not shown). Each of the coupling elements 202 may include a rail element sized and configured to slideably interface with at least one of the slots (or other openings) formed in each of the spiral drive tubes 18. The rail element may include a shape and profile complimentary to and/or configured to couple to a slot (or other opening) formed in each of the spiral drive tubes 18. For example, the slideable coupling elements 202 may include a beam-profile such as a T-beam, I-beam, and/or beam shape and the slot (or other opening) has a complimentary profile configured to couple to the slideable coupling elements 202. Although embodiments are discussed herein including an opening formed in the spiral drive tubes 18 and a complimentary beam profile formed on the slideable coupling elements 202, it will be appreciated that the spiral drive tubes 18 may include a rail element configured to couple to an opening or slot formed in the slideable coupling elements 202. It will be further appreciated that although beam profiles are discussed herein, any suitable slideable coupling element and/or mechanism may be used to slideably couple the slidable coupling elements 202 to the spiral drive tubes 18.

In some embodiments, the first spiral drive tube 18a and the second spiral drive tube 18b may each be coupled to a first slideable coupling element 202a and/or a second slideable coupling element 202b. A spacing 204 defined between the first spiral drive tube 18a and the second spiral drive tube 18b may be adjusted by sliding one or both of the spiral drive tubes 18 towards and/or away from a central point of a slideable coupling element 202a, 202b.

In some embodiments, the spacing 204 between the first spiral drive tube 18a and the second spiral drive tube 18b is adjusted to correspond to a diameter of an allograft 102 to be positioned between the first spiral drive tube 18a and the second spiral drive tube 18b. For example, in various embodiments, the size of an allograft 102 may be determined during a procedure by a surgeon. If a larger or smaller than expected allograft 102 is required, the auto-suture device 10b may be adjusted to accommodate the new size of allograft 102.

In some embodiments, the spacing 204 between sidewalls 38a, 38b is adjusted to couple an allograft 102 to the spiral drive mechanism 12b. For example, the spacing 204 between the first spiral drive tube 18a and the second spiral drive tube 18b may be adjusted such that the distance between the sidewalls 38a, 38b is greater than or equal to a diameter of an allograft 102 to be inserted between the spiral drive tubes 18. The allograft 102 may be at least partially positioned between the first spiral drive tube 18a and the second spiral drive tube 18b. Subsequently, one or both of the spiral drive tubes 18 may be slideably adjusted to reduce the spacing 204 such that the distance between the sidewalls 38a, 38b is less than or equal to the diameter of the allograft 102. In some embodiments, the allograft 102 may be partially compressed prior to and/or simultaneously with insertion of the allograft 102 between the spiral drive tubes 18.

Figure 22:
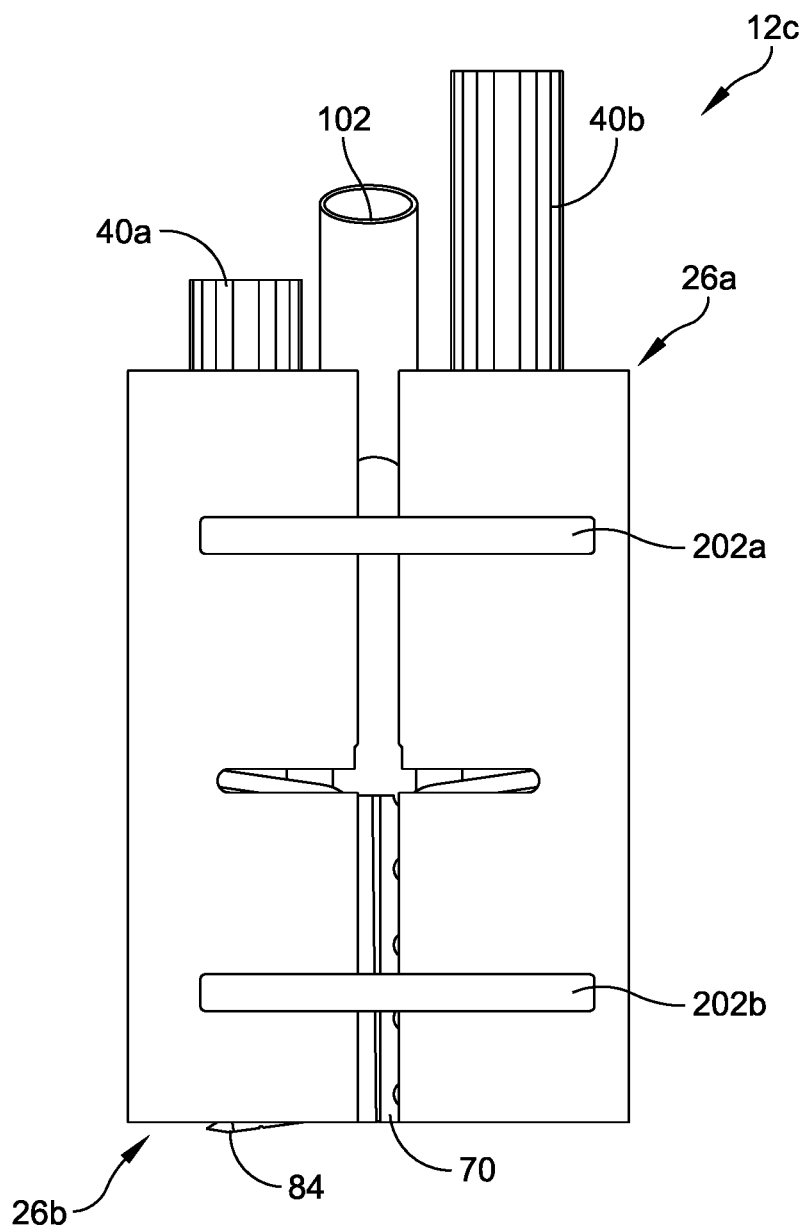
FIG. 22 illustrates a bottom view of an auto-suture device including a spiral drive mechanism having an adjustable spacing, in accordance with some embodiments.
Figure 23:
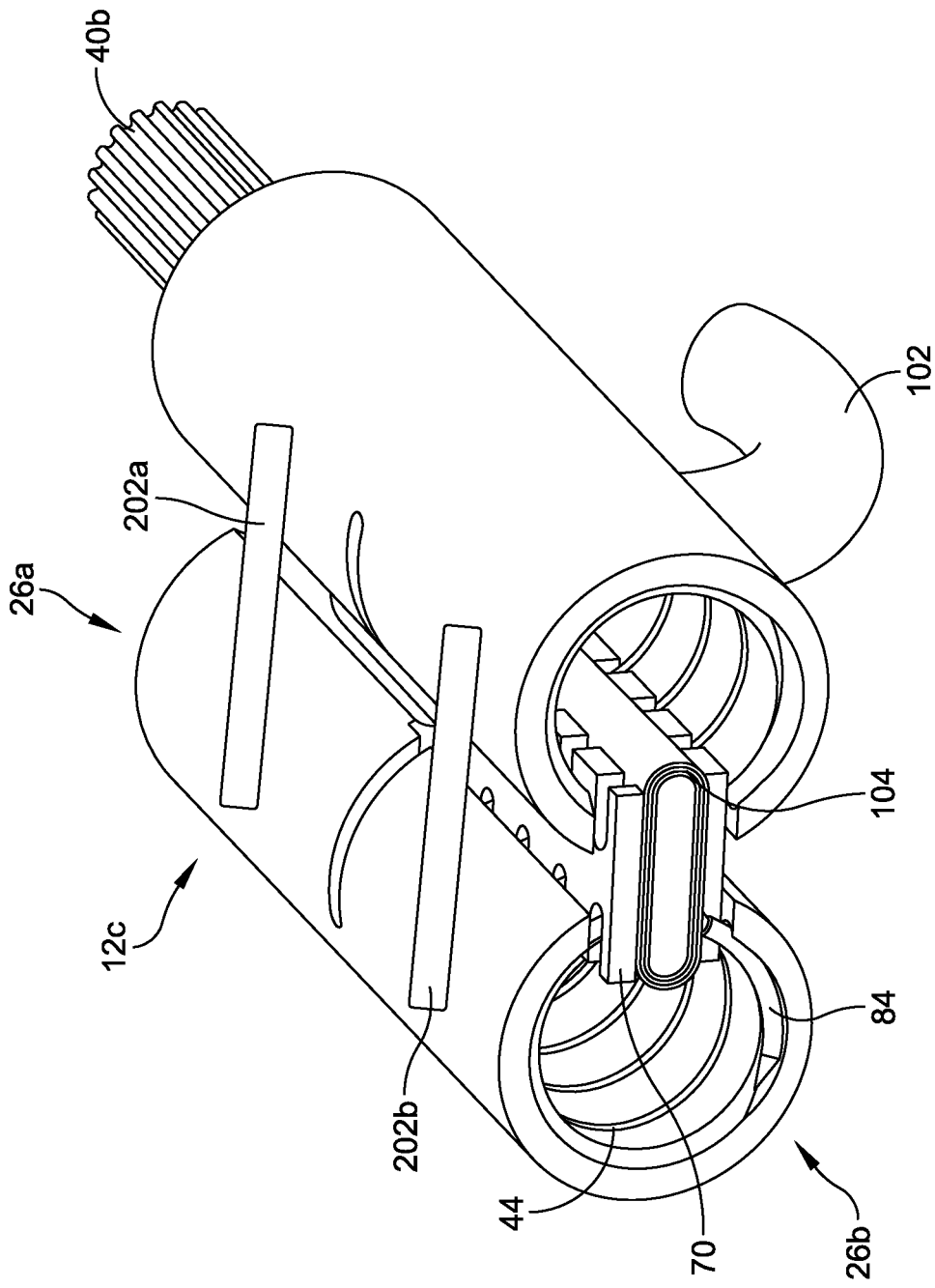
FIG. 23 illustrates a perspective view of the spiral drive mechanism of FIG. 22, in accordance with some embodiments.

FIGS. 22-23 illustrate a spiral drive mechanism 12c having an adjustable spacing, in accordance with some embodiments. The spiral drive mechanism 12c is similar to the spiral drive mechanism 12b discussed above, and similar description is not repeated herein. The spiral drive mechanism 12c includes a first spiral drive tube 18a coupled to a second spiral drive tube 18b by a first slideable coupling element 202a and a second slideable coupling element 202b each coupled to a first side 204 of the spiral drive mechanism 12b. Although embodiments are illustrated having slideable coupling elements positioned only on opposite sides of a spiral drive mechanism (FIG. 21) and the same side of a spiral drive mechanism (FIGS. 22-23), it will be appreciated that a spiral drive mechanism may include slidable coupling elements positioned on the same side and on opposite sides, in accordance with some embodiments.

Although the subject matter has been described in terms of exemplary embodiments, it is not limited thereto. Rather, the appended claims should be construed broadly, to include other variants and embodiments, which may be made by those skilled in the art.

What is claimed is:

1. An auto-suture device, comprising:
    a spiral drive mechanism comprising:
        a first spiral drive tube comprising a cylindrical body having an internal surface defining a first travel path;
        a second spiral drive tube moveably coupled to the first spiral drive tube, the second spiral drive tube comprising a cylindrical body having an internal surface defining a second travel path, the spiral drive mechanism further including;
        a second spiral drive element comprising a drive interface and a needle drive that is sized and configured to be received within the second travel path defined by the second spiral drive tube;
        a first gear cap coupled to the first spiral drive tube; and
        a second gear cap coupled to the second spiral drive tube, the first gear cap and the second gear gap being operatively coupled such that rotation of the first gear cap causes rotation of the second gear cap, with each of the first gear cap and the second gear cap defining an opening having a first locking pattern so that an interface of each of the first spiral drive tube and the second spiral drive tube defines a second locking pattern configured to interface with the first locking pattern; and
    a first spiral drive element comprising a drive interface and a needle drive, wherein the needle drive is sized and configured to be received within the first travel path defined by the first spiral drive tube.

2. The auto-suture device of claim 1, comprising a handle configured to be fixedly coupled to the drive interface of the first spiral drive tube.

3. The auto-suture device of claim 1, comprising a needle coupled to a distal portion of the needle drive of the first spiral drive element.

4. The auto-suture device of claim 3, comprising a needle capture element coupled to a distal end of the first spiral drive tube.

5. The auto-suture device of claim 4, wherein the needle capture element comprises a capture cap.

6. The auto-suture device of claim 1, wherein the first spiral drive tube is moveably coupled to the second spiral drive tube by a pivot element.

7. The auto-suture device of claim 1, wherein the first spiral drive tube is moveably coupled to the second spiral drive tube by at least one slideable coupling element.

8. The auto-suture device of claim 1, wherein the first spiral drive tube defines a suture opening sized and configured to receive a suture therethrough.

9. The auto-suture device of claim 1, wherein the spiral drive mechanism comprises:
    a moveable compression plate configured to be moved from a first position to a second position; and
    a fixed compression plate.

10. The auto-suture device of claim 9, wherein the moveable compression plate comprises a perimeter surface defining a plurality of cutouts sized and configured to receive a needle therethrough.

11. The auto-suture device of claim 1, wherein the first spiral drive tube comprises a first sidewall and the second spiral drive comprises a second sidewall, and wherein the first sidewall and the second sidewall are configured to define an allograft channel therebetween.

12. An auto-suture device, comprising:
    a spiral drive mechanism comprising:
        a first spiral drive tube comprising a cylindrical body having an internal surface defining a first travel path;
        a second spiral drive tube comprising a cylindrical body having an internal surface defining a second travel path, wherein the first spiral drive tube is coupled to the second spiral drive tube by a pivot element;
        a first spiral drive element comprising a drive interface and a needle drive, wherein the needle drive of the first spiral drive element is sized and configured to be received within the first travel path defined by the first spiral drive tube;
        a second spiral drive element comprising a drive interface and a needle drive, wherein the needle drive of the second spiral drive element is sized and configured to be received within the second travel path defined by the second spiral drive tube;
    a first gear cap rotatably coupled to the interface of the first spiral drive element;

a second gear cap rotatably coupled to the interface of the second spiral drive element and operatively coupled to the first gear cap so that rotation of a handle that is fixedly coupled to the drive interface, about an axis of rotation, causes simultaneous rotation of the first gear cap and the second gear cap thereby causing simultaneous advancement of the first spiral drive element and the second spiral drive element within the first travel path and the second travel path, respectively, and further wherein each of the first gear cap and the second gear cap define an opening having a first locking pattern so that the interface of each of the first spiral drive tube and the second spiral drive tube define a second locking pattern configured to interface with the first locking pattern.

13. The auto-suture device of claim 12, comprising:
a first needle coupled to a distal end of the first spiral drive element; and
a second needle coupled to a distal end of the second spiral drive element.

14. The auto-suture device of claim 12, comprising:
a moveable compression plate configured to be moved from a first position to a second position; and
a fixed compression plate.

15. A method of suturing an allograft, comprising:
providing an auto-suture device including a spiral drive mechanism comprising a first spiral drive tube comprising a cylindrical body having an internal surface defining a first travel path; a second spiral drive tube moveably coupled to the first spiral drive tube the second spiral drive tube comprising a cylindrical body having an internal surface defining a second travel path, wherein the spiral drive mechanism includes a second spiral drive element comprising a drive interface and a needle drive, wherein the needle drive of the second spiral drive element is sized and configured to be received within the second travel path defined by the second spiral drive tube; a first gear cap coupled to the first spiral drive tube; and a second gear cap coupled to the second spiral drive tube, the first gear cap and the second gear gap being operatively coupled such that rotation of the first gear cap causes rotation of the second gear cap, whereby each of the first gear cap and the second gear cap define an opening having a first locking pattern so that the interface of each of the first spiral drive tube and the second spiral drive tube define a second locking pattern configured to interface with the first locking pattern, and a first spiral drive element comprising a drive interface and a needle drive, wherein the needle drive is sized and configured to be received within the first travel path defined by the first spiral drive tube;
positioning a portion of an allograft between the first spiral drive tube and the second spiral drive tube of the spiral drive mechanism;
rotating the first spiral drive element within the first spiral drive tube to advance the first spiral drive element along the travel path defined by an inner surface of the first spiral drive tube;
coupling a suture to the portion of the allograft positioned between the first spiral drive tube and the second spiral drive tube, wherein rotation of the spiral drive element causes a needle to penetrate the allograft, and wherein the suture is coupled to the needle; and
releasing the allograft from the spiral drive mechanism by pivoting the first spiral drive tube and the second spiral drive tube.

16. The method of claim 15, comprising compressing the portion of the allograft positioned between the first spiral drive tube and the second spiral drive tube prior to coupling the suture to the allograft, wherein the allograft is compressed by a moveable compression plate.

* * * * *